US010363233B2

(12) United States Patent
Wright et al.

(10) Patent No.: US 10,363,233 B2
(45) Date of Patent: *Jul. 30, 2019

(54) GRANULAR FEED SUPPLEMENT

(71) Applicant: H.J. BAKER & BRO., LLC, Shelton, CT (US)

(72) Inventors: Danny R. Wright, Buford, GA (US); Richard J. Valagene, Republic, MO (US)

(73) Assignee: H. J. BAKER & BRO., LLC, Shelton, CT (US)

( * ) Notice: Subject to any disclaimer, the term of this patent is extended or adjusted under 35 U.S.C. 154(b) by 222 days.

This patent is subject to a terminal disclaimer.

(21) Appl. No.: 15/136,669

(22) Filed: Apr. 22, 2016

(65) Prior Publication Data

US 2016/0235700 A1 Aug. 18, 2016

Related U.S. Application Data

(63) Continuation of application No. 13/275,895, filed on Oct. 18, 2011.

(60) Provisional application No. 61/394,057, filed on Oct. 18, 2010.

(51) Int. Cl.
*A61K 9/50* (2006.01)
*A61K 9/00* (2006.01)
*A23K 40/35* (2016.01)
*A23K 50/10* (2016.01)
*A23K 20/142* (2016.01)
*A23K 20/158* (2016.01)
*A61K 31/198* (2006.01)

(52) U.S. Cl.
CPC .......... *A61K 31/198* (2013.01); *A23K 20/142* (2016.05); *A23K 20/158* (2016.05); *A23K 40/35* (2016.05); *A23K 50/10* (2016.05); *A61K 9/0056* (2013.01); *A61K 9/5015* (2013.01); *A61K 9/5089* (2013.01)

(58) Field of Classification Search
CPC .. A61K 31/198; A61K 9/0056; A61K 9/5015; A61K 9/5089; A23K 20/142; A23K 20/158; A23K 40/35; A23K 50/10
See application file for complete search history.

(56) References Cited

U.S. PATENT DOCUMENTS

| | | | |
|---|---|---|---|
| 3,541,204 A | 11/1970 | Sibbald et al. | |
| 3,655,864 A * | 4/1972 | Grass et al. | A61K 9/1617 424/438 |
| 3,804,776 A | 4/1974 | Yazawa et al. | |
| 3,959,493 A | 5/1976 | Baalsrud et al. | |
| 4,642,317 A | 1/1987 | Palmquist et al. | |
| 4,713,245 A | 12/1987 | Ando et al. | |
| 4,808,412 A | 2/1989 | Smith et al. | |
| 4,832,967 A | 5/1989 | Autant et al. | |
| 4,876,097 A | 10/1989 | Autant et al. | |
| 4,937,083 A * | 6/1990 | Itagaki | A23K 40/35 426/302 |
| 5,093,128 A | 3/1992 | Draguesku et al. | |
| 5,145,695 A | 9/1992 | Smith et al. | |
| 5,190,775 A * | 3/1993 | Klose | A61K 9/501 424/438 |
| 5,227,166 A | 7/1993 | Ueda et al. | |
| 5,429,832 A * | 7/1995 | Ueda | A61K 9/5015 424/438 |
| 5,496,571 A | 3/1996 | Blagdon et al. | |
| 5,585,134 A * | 12/1996 | Cummings | A23K 20/147 424/438 |
| 5,676,966 A | 10/1997 | Kitamura et al. | |
| 5,714,185 A | 2/1998 | Mahadevan | |
| 5,720,970 A | 2/1998 | Rode et al. | |
| 5,807,594 A | 9/1998 | King et al. | |
| 6,017,555 A | 1/2000 | Stevens et al. | |
| 6,022,566 A | 2/2000 | Miller | |
| 6,229,031 B1 | 5/2001 | Strohmaier et al. | |
| 6,238,727 B1 | 5/2001 | Takemoto et al. | |
| 6,242,013 B1 | 6/2001 | Luhman et al. | |
| 6,468,562 B2 * | 10/2002 | Moilanen | A61K 8/44 424/490 |
| 6,797,291 B2 | 9/2004 | Richardson | |
| 7,939,117 B2 * | 5/2011 | Zuccarello | A23K 40/10 426/2 |
| 2002/0127259 A1 | 9/2002 | Orthoefer | |
| 2003/0129295 A1 | 7/2003 | Richardson | |
| 2003/0148013 A1 | 8/2003 | Jobe et al. | |
| 2005/0019413 A1 | 1/2005 | Cavassini et al. | |
| 2006/0067984 A1 | 3/2006 | Cavassini et al. | |

(Continued)

FOREIGN PATENT DOCUMENTS

CN 1091905 A 9/1994
EP 0940088 A2 9/1999

(Continued)

OTHER PUBLICATIONS

Non-Final Office action dated May 13, 2011, in U.S. Appl. No. 12/285,064, 8 pages.
Non-Final Office Action dated May 13, 2011, in U.S. Appl. No. 12/662,486, 11 pages.
Chinese Office Action dated Jan. 31, 2012, for Chinese Application No. 200880111092.3, 18 pages.
International Preliminary Report on Patentability and Written Opinion dated Apr. 23, 2013 for International Application No. PCT/US2011/056675, 8 pages.

(Continued)

*Primary Examiner* — C. Sayala
(74) *Attorney, Agent, or Firm* — Dorsey & Whitney LLP

(57) ABSTRACT

A ruminant feed composition, having a granulated core having at least one active substance and at least one layer of a coating material surrounding the core, the coating material comprising one or more linear, saturated aliphatic monocarboxylic acids in an amount of at least 60 wt % of the total weight of the coating material.

21 Claims, No Drawings

(56) References Cited

U.S. PATENT DOCUMENTS

| | | | |
|---|---|---|---|
| 2007/0231369 A1 | 10/2007 | Hargrove | |
| 2008/0008779 A1* | 1/2008 | Zuccarello | A23K 40/10 |
| | | | 426/2 |
| 2009/0092704 A1 | 4/2009 | Gately et al. | |
| 2010/0272852 A1 | 10/2010 | Wright et al. | |

FOREIGN PATENT DOCUMENTS

| | | | |
|---|---|---|---|
| EP | 1405570 A1 | 4/2004 | |
| EP | 1741347 A1 | 1/2007 | |
| JP | 60141242 A | 7/1985 | |
| JP | 60168351 | 8/1985 | |
| JP | 61195653 | 8/1986 | |
| JP | 63317053 | 12/1988 | |
| WO | 96/08168 A1 | 3/1996 | |
| WO | WO 2006032958 A2 * | 3/2006 | A61K 9/1611 |
| WO | 2008/015203 A2 | 2/2008 | |
| WO | 2010/123878 A1 | 10/2010 | |

OTHER PUBLICATIONS

International Search Report and Written Opinion dated Feb. 10, 2012, for International Application No. PCT/US2011/056675, 11 pages.
International Search Report and Written Opinion dated Jun. 4, 2010, for International Application No. PCT/US2010/031724, 9 pages.
Office Action dated Dec. 5, 2013, for U.S. Appl. No. 13/431,790, 16 pages.
PCT Written Opinion dated Jan. 21, 2009, PCT Application No. PCT/US2008/011266 filed Sep. 29, 2008, 6 pages.
Watanabe, Kazumasa et al., "Effects of Fat Coated Rumen Bypass Lysine and Methionine on Performance of Dairy Cows Fed a Diet Deficient in Lysine and Methionine," *Animal Science Journal*, (2006), vol. 77, 8 pages.

* cited by examiner

GRANULAR FEED SUPPLEMENT

This nonprovisional application claims the benefit of U.S. Provisional Application No. 61/394,057, filed Oct. 18, 2010 and is a continuation of U.S. application Ser. No. 13/275,895, filed Oct. 18, 2011, now U.S. Pat. No. 10,092,533.

BACKGROUND

This disclosure is generally directed to granular feed supplements for ruminant animals. In particular, this disclosure provides a granular feed supplement for a ruminant in which a physiologically active substance is stable in the rumen of a ruminant animal and is digested and absorbed in the abomasum and subsequent digestive tract. Also disclosed are a method of making and a method of using the granular feed supplement.

Ruminant animals are mammals of the suborder Ruminantia that have a stomach divided into four morphologically distinct compartments: the rumen, the reticulum, the omasum, and the abomasum. The rumen and the reticulum are derived from the terminal portion of the esophagus, and only the omasum and the abomasum are considered to be a genuine stomach. Bacteria present in the rumen enable ruminants to digest cellulosic materials such as grass. Conventional digestion occurs in the abomasum, sometimes called the "true stomach." Well-known ruminants include cattle, sheep, and goats.

The rumen, which is essentially a continuous fermenter, supports a variety of micro-organisms under neutral conditions which attack and digest much of the ingested feedstuffs consumed by a ruminant as part of their normal life cycle. Ingested protein material is broken down in the rumen to soluble peptides and amino acids that are used as nutrients by the microorganisms. A stream of ingesta, rich in microbial cells, passes out of the rumen into the omasum. The function of the omasum is to separate liquids and solids. Much of the liquid reenters the rumen while the remainder of the material enters the abomasum. Digestion and absorption then proceed in the abomasum in a manner similar to that found in monogastrics. Enzymes secreted into the lumen of the abomasum digest much of the material, including the microbial cells. The digested microbial cells provide protein and amino acids to the ruminant.

The microbial action of the rumen has the great advantage of being able to convert many feed components which have no direct nutritive value for the host into products which can be assimilated and utilized by the host. For example, urea may be converted to microbial protein which subsequently may be digested and utilized by the host animal. Cellulose may be converted to a mixture of volatile fatty acids which can serve as a source of energy to the host.

Unfortunately, this microbial action also presents certain disadvantages. For instance, soluble proteins of high nutritive value may be broken down and digested in the rumen and in part resynthesized into microbial protein of lower nutritive value. Amino acids are also chemically changed by the rumen microorganisms, which convert amino acids to carbon dioxide, volatile fatty acids, and ammonia.

All proteins present in animals are constituted by combinations of more than 20 different amino acids. Among these, ten "essential" amino acids are not adequately synthesized in the animal body, and the animals must take them in. When essential amino acids are lacking in the ruminant diet the ruminant's health, milk production, etc., are all negatively affected.

It is common practice in ruminant production to supply biologically active substances in the daily diet of the animals in order to improve their conditions of health and their productive performance. Active substances of interest include amino acids, vitamins, enzymes, nutrients such as proteins and carbohydrates, probiotic micro-organisms, prebiotic foods, mineral salts, choline, etc. Some of these substances are already normally present in foods used for feeding animals. Sometimes the amount of essential active substances present in the diet may be insufficient or inadequate to cope with states of deficiency or situations of high productivity. Therefore, it is desirable to carefully formulate or supplement the daily diet of ruminant animals in order to address these concerns.

However, when physiologically active substances such as amino acids and proteins are orally fed, a substantial part of the substance (e.g., proteins, amino acids, etc.) are decomposed by microorganisms in the rumen, making it difficult or impossible for the animal to effectively utilize all of the administered proteins and amino acids contained in feed, etc. Thus, essential amino acids are destroyed and rendered unavailable for animal production. Animal production is limited by the supply of individual essential amino acids that escape, or bypass, the rumen intact and reach the lower gastrointestinal tract where they can be absorbed and become available for animal production.

Accordingly, it is important to pass the biologically active substances through the rumen without decomposition by microorganisms to allow the biologically active substances to be effectively digested and absorbed in the abomasum and subsequent digestive tract. Consequently, a great deal of effort has been expended towards providing a bioactive substance in a form which will pass through the rumen essentially unaltered, yet undergo disintegration and absorption in the abomasum.

There are numerous methodologies that are designed to increase the amount of a nutrient that passes through the rumen without being degraded by the rumen microflora, thereby delivering a larger portion of that nutrient to the lower gastrointestinal tract, including: heat and chemical treatment, encapsulation and coating, use of amino acid analogs, and polymeric compounds of amino acids.

For instance, it has been proposed to coat ruminant animal feed additives containing biologically active substances with protective substances, such as fatty acids, hardened animal oils, and hardened vegetable oils. However, particles coated with these fats and oils are stable not only in the rumen, but also in the abomasum and subsequent digestive tract, making the biologically active substances difficult to be released in the abomasum and subsequent digestive tract.

Another method proposed utilizes the difference in pH between the rumen and the abomasum by coating with a polymer that is insoluble in the environment of the rumen but is soluble in the strongly acidic abomasum. Such polymers include polyvinylpyrrolidone, polyamides, and celluloses that have been chemically modified. This solution has the drawback of a high production cost, combined with the fact that using synthetic polymers introduces non-physiological substances into the animals' diet. Such polymer coating products thus require FDA approval.

A few patents disclose coating biologically active substances with material that allegedly survives the rumen but degrades in the abornasum.

For example, U.S. Pat. No. 3,541,204 discloses hydrogenated vegetable and animal fats and waxes such as rice bran wax as coatings that survive the rumen but are disrupted in the intestinal tract.

U.S. Pat. No. 3,959,493 describes utilizing aliphatic fatty acids having at least 14 carbon atoms each. The fatty acids are applied as a coating to an individual nutrient. The fatty acids are said to be resistant to rumen degradation. The active agents then are delivered to the abomasum and/or intestine where the fatty acids are reduced in the post-ruminal environment.

U.S. Pat. No. 4,642,317 describes a process for supplying fatty acids to ruminants in the form of their calcium salts. However, the sole use of fatty acid salts as feed additives creates a distinctly disagreeable odor from the oxidation of the organic volatiles in the feed causing a reduction in feed intake and milk yield.

U.S. Pat. No. 4,713,245 discloses a rumen-surviving granule comprising a core of bioactive material, a coating substance stable at neutral pH (as found in the rumen) but dissolved or disintegrated at pH=3 (as found in the abomasum), and at least one other coating selected from the group consisting of fatty acids having at least 14 carbon atoms and waxes, animal fat, and vegetable fat having a melting point of 40° C. or higher.

U.S. Pat. No. 4,808,412 describes a rumen stable composition containing an active agent molecularly dissolved with a basic polymer. The active agent is delivered post-ruminally because the polymer is resistant to a pH of greater than about 5, but is soluble or swellable at a pH of less than about 3.5. In this type of dispersion, some of the active agent at and near the surface of the composition will be destroyed by the action of ruminal microbes because cracks or channels can occur on the surface, reducing the effectiveness of the protection.

U.S. Pat. No. 4,832,967 discloses a two-layer rumen-surviving coating for water-soluble bioactive substances. The resulting particulate is stable at pH at least as high as 5.5, and releases bioactive substance at pH of 3.5 or less. The coating medium comprises an inner first coating layer consisting of material sensitive to pH variations and an outer second coating layer consisting of a hydrophobic composition that must include inorganic filler if the bioactive core has not undergone a surface treatment (application of hydrophobic binder). This hydrophobic outer coating layer is provided with a texture that permits diffusion or penetration of the external liquid medium. The outer coating preferably contains a mixture of hydrophobic substances.

U.S. Pat. No. 4,876,097 discloses a coating composition that is stable at pH less than or equal to about 3.5. The coating comprises a film-forming, water-insoluble binder that contains a substance that controls hydrophilicity, and optionally a substance that is sensitive to pH. Both waxes (hydrophobic) and propylene glycol (water-soluble) are suitable for controlling the hydrophilic/hydrophobic balance. Controlling the hydrophilicity of the particle is said to limit release of the bioactive material in neutral or slightly acidic media, i.e., in the rumen. In very acidic media, i.e., the abomasum, pH-sensitive fillers are activated by the media, which diffuses slowly at a rate established by the hydrophilicity of the coating. The resulting dissolution or swelling of the pH-sensitive filler degrades the coating and releases the bioactive material.

U.S. Pat. No. 5,093,128 describes a beadlet nutrient coating that includes fats and calcium based products. Coated ruminant nutrients have the disadvantage of cracking or abrading either in handling or in being masticated by the animal.

U.S. Pat. No. 5,145,695 provides a method wherein a particular feed composition that delivers an improved balance of essential amino acids post-ruminally is fed to a cow.

U.S. Pat. No. 5,227,166 discloses a feed supplement for ruminants consisting of a coated biologically active substance, such as an amino acid, drug, or vitamin. The coating composition comprises lecithin, at least one inorganic substance which is stable in neutrality and soluble under acidic conditions, and at least one substance selected from the group consisting of straight-chain or branched-chain saturated or unsaturated monocarboxylic acids having 14 to 22 carbon atoms, salts thereof, hardened vegetable oils, hardened animal oils, and waxes.

U.S. Pat. No. 5,496,571 discloses a method of encapsulating choline to produce a rumen bypass supplement for ruminants. This type of encapsulation produces spherical particles having a core of choline surrounded by a shell of fat. Encapsulation is a relatively expensive manufacturing process. Furthermore, the high degree of saturation of the fat needed for solidification tends to reduce the digestibility of the choline.

U.S. Pat. No. 5,714,185 describes a scheme for treating protein substances with zein/formaldehyde to render the ingredients protected from rumen degradation. However, formaldehyde results in the destruction and reduced bioavailability of most essential amino acids. Broderick, G. A. et al., "Control of rate and extent of protein degradation," Physiological Aspects of Digestion and Metabolism in Ruminants, Tsuda et al., eds., p. 541, 1991; Academic Press, London. Furthermore, the level of formaldehyde sometimes used is too high, creating health concerns associated with its carcinogenicity and has not been approved by the FDA for animal feed applications.

U.S. Pat. No. 5,807,594 describes a method of improving weight gain and feed efficiency in a ruminant by encapsulating a choline chloride composition in a rumen-protected carrier. Suitable encapsulating or coating materials for use in this invention include hydrogenated oils, mono- and di-glycerides, waxes, and seed fats.

U.S. Pat. No. 6,022,566 describes the addition of fat to a feed ration and then adding rumen protected encapsulated choline chloride in an amount proportional to the added fat. However, such coatings and encapsulations of choline chloride are subject to abrasion, cracking, and other abuses during transport and handling, thereby rendering the coatings permeable to rumen fluids and microorganisms that destroy the choline.

U.S. Pat. No. 6,229,031 describes a method for manufacturing feed supplements by converting lipids that are byproducts of the food and meat processing industries to their calcium salt form.

U.S. Pat. No. 6,242,013 describes a ruminally-protected high oleic material produced by roasting oilseeds at high temperatures to protect the fatty acids fed to ruminants. However, the roasting procedures require costly energy consumption.

U.S. Patent Application Publication No. 2002/0127259 indicates that coated ruminant nutrients are disadvantageous due to cracking or abrading either in handling or in being masticated by the animal.

Japanese Laid-Open Patent Publication No. 60-168351 proposes a method of dispersing a biologically active substance in a protective substance which comprises granulating a biologically active substance containing at least 20% by weight of calcium carbonate and at least 10% by weight of a substance selected from the group consisting of monocarboxylic acid, a hardened oil and fat.

Japanese Laid-Open Patent Publication No. 61-195653 proposes a process for dispersing a biologically active substance in coating materials composed of at least 10% by weight of a substance selected from the group consisting of a monocarboxylic acid, a hardened oil and fat, and at least 20% by weight to not more than 50% by weight of an insoluble salt of an acid which is more weakly acidic than hydrochloric acid.

Japanese Laid-Open Patent Publication No. 63-317053 describes a method that comprises coating a biologically active substance with a coating material containing the protective substance composed of a monocarboxylic acid, hardened oil, lecithin, and a glycerin fatty acid ester.

WO 96/08168 describes a ruminant feedstuff to improve milk yields in dairy cattle. The feedstuff is composed of a rumen-protected choline compound having a protective coating containing at least one fatty acid or fatty acid soap.

Watanabe et al. (K. Watanabe et al., "Effects of fat coated rumen bypass lysine and methionine on performance of dairy cows fed a diet deficient in lysine and methionine," Animal Science Journal, 77:495-502, 2006) report that the present technology to produce rumen protected amino acids has been limited to methionine. Watanabe et al. further report on the significant challenges of developing a rumen protected lysine, due to its physical and chemical properties. Watanabe et al. also indicate that from an industrial point of view, it was only worthwhile establishing rumen protected technology with hydrogenated fat and/or minerals, which are already registered as feed ingredients. Watanabe et al. disclose the bioavailability of fat coated rumen protected L-lysine hydrochloride in lactating dairy cows and the effect of rumen protected L-lysine hydrochloride and rumen protected methionine on lactation performance of high-yielding dairy cows fed a silage-based practical diet. Watanabe et al. report that the intestinal availability of their fat coated rumen protected lysine was calculated to be 66.2%.

In view of the foregoing problems, the need still exists to provide a feed supplement that protects a biologically active substance stably in the rumen of a ruminant animal and yet allows the effective digestion and absorption in the abomasum and subsequent digestive tract of the active substance.

SUMMARY

The present disclosure addresses these and other needs by providing an improved composition containing a biologically active substance that can effectively be digested, absorbed, and utilized by ruminant animals while being a safe and economical product.

Disclosed is a ruminant feed composition, comprising a granulated core material comprising at least one biologically active substance and a coating material surrounding the core material. The coating material may comprise saturated, linear aliphatic monocarboxylic acids having from 2 to 34 carbon atoms, in an amount of at least 60 wt % of the total weight of the coating material.

Also disclosed is a method of providing an amino acid to a ruminant, comprising providing the amino acid in a granular core coated with a coating material and including the coated granule in a feed that is fed to the ruminant.

DETAILED DESCRIPTION OF EMBODIMENTS

This disclosure relates to feed additives comprising a core that is coated with a coating material, which are stable in the rumen of a ruminant animal and are digested and absorbed in the abomasum and subsequent digestive tract.

The core comprises at least one granulated physiologically active substance or biologically active substance (hereinafter "active substance"). The core may be a single granule, or may further include a matrix comprising one or more excipients such as binding substances, inert ingredients, and flow-control substances that together aid the formation of pellets of granulated active substances. The core may comprise one or more active substances, generally in a solid form, and must be firm enough so as to remain intact during the following phases of processing, especially during coating operations.

The term "active substance" herein refers to, for example, amino acids, vitamins, enzymes, nutrients such as proteins and carbohydrates, probiotic micro-organisms, prebiotic foods, mineral salts, mixes of acids such as for instance lactic acid, fumaric acid, citric acid and malic acid, choline, and choline derivatives. These active substances may be used individually, or mixed together in varying weight ratios.

Specifically, the active substances may include, for example: amino acids such as lysine, methionine, tryptophan, arginine, histidine, isoleucine, leucine, phenylalanine, valine, and threonine; amino acid derivatives such as N-acylamino acid and N-hydroxymethylmethionine calcium salt, lysine sulfate, and lysine hydrochloride; hydroxy homologous compounds of amino acids such as 2-hydroxy-4-methylmercaptobutyric acid and salts thereof; powders of natural nutrients such as grain powders, and feathers; proteins such as casein, corn proteins, and potato proteins; carbohydrates such as starch, cane sugar, and glucose; vitamins and substances having a similar function such as vitamin A, vitamin A acetate, vitamin A palmitate, vitamins B, thiamine, thiamine hydrochloride, riboflavin, nicotinic acid, nicotinic acid amide, calcium pantothenate, choline pantothenate, pyridoxine hydrochloride, choline chloride, cyanocobalamine, biotin, folic acid, p-aminobenzoic acid, vitamin $D_2$, vitamin $D_3$, and vitamin E; antibiotics such as tetracyclic antibiotics, amino glycoside antibiotics, macrolide-type antibiotics, polyethertype antibiotics; insecticides such as negfon; vermicides such as piperazine; and hormones such as estrogen, stibestrol, hexestrol, tyroprotein, and goitrogen.

Several active substances have been identified that aid in improving milk and meat production of ruminant animals, including the amino acids lysine and methionine. When used in dietary supplements, different salt forms of such amino acids may be used to supply the desired amino acid. For example, lysine may be in the form of lysine hydrochloride or lysine sulfate. In addition, the physical characteristics of the amino acid salt may range from very fine, almost powdery, to large granules. Therefore, the chemical and physical properties of the final product, and thus its ability to bypass the rumen and be effectively metabolized by the ruminant animal, are directly related to the amino acid salt selected.

A preferred form of lysine is a granulated L-lysine sulfate having the following attributes. The particle size is preferably in the range of about 0.3 mm to about 3.0 mm, and more preferably is in the range of about 0.3 mm to about 1.0 mm, or in the range of about 1.0 mm to about 2.0 mm, or in the range of about 2.0 mm to about 3.0 mm, or in the range of about 0.3 mm to about 1.6 mm, or in the range of about 0.8 mm to about 1.2 mm.

The granulated L-lysine sulfate may be screened before being coated to eliminate fine particles. For example, at least 99%, or at least 99.2%, or at least 99.4%, or at least 99.6%, or at least 99.8%, or 100% of the granulated. L-lysine sulfate particles have a particle size greater than 300 µm, or 400 µm, or 500 µm, or 600 µm, or 700 µm, or 800 µm.

The lysine assay may be 50% minimum. The moisture content may be 5% maximum, and the bulk density may be 0.70±0.07 grams/cc. Such a lysine product is commercially available as BIOLYS® manufactured by Evonik Corporation.

The coating materials for coating a core containing the active substance may comprise linear or branched aliphatic monocarboxylic acids having from 2 to 34 carbon atoms, such as, for example, from 2 to 24 carbon atoms, or from 10 to 34 carbon atoms, or from 14 to 22 carbon atoms, or from 16 to 20 carbon atoms. The aliphatic monocarboxylic acids may be saturated or unsaturated. Unsaturated aliphatic monocarboxylic acids may have 1, 2, 3, 4, or more double bonds, where each double bond is independently in the cis or trans conformation. As used herein, "aliphatic monocarboxylic acid" includes aliphatic monocarboxylic acids that are in free form, salts of aliphatic monocarboxylic acids, and esterified aliphatic monocarboxylic acids, such as a mono-, di-, or triglycerides, and phospholipids.

Aliphatic monocarboxylic acids may be obtained from naturally occurring sources, or may be synthesized. Examples of sources of aliphatic monocarboxylic acids include vegetable oil, animal fat, and waxes. Examples of suitable vegetable oils include palm oil, soybean oil, rapeseed oil, cottonseed oil, and castor oil. The vegetable oil may be partially or fully hydrogenated. Examples of suitable animal fats include beef tallow and lard. The animal fat may be partially or fully hydrogenated. Examples of waxes include carnauba wax, beeswax, paraffin wax, and other natural and synthetic waxes.

The coating material may comprise one or more aliphatic monocarboxylic acids originating from one or more sources, such as the sources described above. Vegetable oils, among other things, contain a mixture of various fatty acids. For example, soybean oil contains about 51% linoleic acid (C18:2), 23% oleic acid (C18:1), 10% palmitic acid (C16), 7% α-linolenic acid, and 4% stearic acid (C18). Hydrogenating oils and fats increases the degree of saturation of the fatty acids, which in turn increases an oil's viscosity and melting point. Another way of increasing the melting point of a coating material comprising aliphatic monocarboxylic acids is to increase the amount of saturated aliphatic monocarboxylic acids present in the coating material. For example, soybean oil may be supplemented with additional palmitic acid (C16) and/or stearic acid (C18) to increase the amount of saturated aliphatic monocarboxylic acids present in the coating material. Other supplemental compounds that may be added to the coating material include oleic acid, lecithin, palm oil, and combinations thereof.

The coating material may comprise from about 60 to 100 wt % linear, saturated aliphatic monocarboxylic acids per total weight of the coating material, or from about 70, 75, 80, 85, or 90 wt % to about 100, 99, 98, 97, 96, 95, 94, 93, 92, or 91 wt % saturated aliphatic monocarboxylic acids per total weight of the coating material.

The linear, saturated aliphatic monocarboxylic acids present in the coating material may consist of or consist essentially of a single linear, saturated aliphatic monocarboxylic acid, such as, for example, stearic acid (c18). Or, the linear, saturated aliphatic monocarboxylic acids present in the coating material may comprise a mixture of two or more linear, saturated aliphatic monocarboxylic acids. For example, the coating material may comprise a mixture of stearic acid and palmitic acid in a ratio of from 20:1 to 3:1 parts of stearic acid to palmitic acid by weight. The mixture of stearic acid and palmitic acid may account for 90 wt % or more of the total weight of linear, saturated aliphatic monocarboxylic acids present in coating material, such as about 91, 92, 93, 94, 95, 96, 97, 98, 99, or 100 wt % of the total weight of linear, saturated aliphatic monocarboxylic acids present in coating material, although amounts below 90 wt % may also be used.

The coating material should have a melting temperature in the range of from about 40° C. to about 80° C., such as in the range of about 50° C. to about 60° C., or in the range of about 60° C. to about 70° C., or in the range of about 70° C. to about 80° C., or in the range of about 55° C. to about 65° C., or in the range of about 60° C. to about 75° C., to ensure that the coating on the final product has a hard surface, thereby preventing agglomeration of the final product, and also to increase the stability of the product in the rumen.

Fully hydrogenated and some partially hydrogenated vegetable oils contain a high percentage of linear, saturated aliphatic monocarboxylic acids. In some embodiments, fully hydrogenated soybean oil is used in the coating material. Such a hydrogenated soybean oil is commercially available as Runge Oil Soybean Flakes manufactured by Bunge, Ltd. In some embodiments, hydrogenated rapeseed oil may be used. Such a hydrogenated rapeseed oil is commercially available as AGRIPURE AP-660 manufactured by Cargil (Hamburg, Germany).

As an alternative to using, for example, hydrogenated vegetable oils or hardened animal fats as raw materials for the coating material, one or more free fatty acids may be used as the raw materials. For example, palmitic acid, commercially available as Palmitic Acid 95% FGK from ACME Hardestry (Malaysia) may be mixed with stearic acid, commercially available as Stearic Acid 90% FGK from ACME Hardestry (Malaysia) to obtain a coating material having a high percentage of linear, saturated aliphatic monocarboxylic acids. Other free saturated fatty acids are also commercially available, as well as free unsaturated fatty acids, such as, for example, oleic acid commercially available as Oleic Acid 80% FGK from ACME Hardestry (Malaysia). Of course, there are numerous commercially available sources of aliphatic monocarboxylic acids, including many different grades and purities, that are suitable for the coating material.

The core containing the active substance should be coated with a sufficient amount of coating material to completely coat the core and to obtain a rumen bypass rate of at least 50%, such as at least 55%, or at least 60%, or at least 65%, or at least 70%, or at least 75%, or at least 80%, or at least 85%, or at least 88%, or at least 90%, or at least 93%, or at least 96%. The "rumen bypass rate" is the percentage of the active substance contained in the core before entering the rumen that remains in the core upon exiting the rumen.

The weight percent ratio of the core to the coating material may be in a range of from about 50:50 to about 70:30, such as 50:50, or 55:45, or 60:40, or 65:35, or 70:30. In other embodiments, the weight percent ratio of the core to the coating material is in a range from about 70:30 to about 90:10, such as 75:25, or 80:20, or 85:15, or 90:10.

The $d_{50}$ of the final product may be in the range from about 300 µm to about 5,000 µm. In some embodiments, the $d_{50}$ of the final product may be in the range from about 600 µm to about 3,000 µm, or from about 800 µm to about 1,900 µm, or from about 1,000 µm to about 1,500 µm, from about 1,200 µm to about 1,800 µm.

In addition to exhibiting a rumen bypass rate of at least 50%, the coated core material should also exhibit a sufficient intestinal digestibility rate. The "intestinal digestibility rate" is the percentage of the active substance passed from the rumen that is digested and absorbed in the abomasum and subsequent digestive tract. The intestinal digestibility rate may be at least 70%, or at least 75%, or at least 80%, or at least 85%, such as in the range of 70% to about 100%, or such as in the range of about 80% to about 90%, or in the range of about 90% to about 100%, or in the range of about 85% to about 96%, or in the range of about 89% to about 95%, or in the range of about 93% to about 99%, or in the range of about 75% to about 95%.

The core may be coated by spray coating, pan coating, fluid bed coating, continuous pour coating, or any other method known to those of skill in the art. This may be done in a batch or in a continuous process. The core may be coated with a single layer of the coating material applied in a single coating application, or the core may be coated with multiple layers of coating material, such as, for example, 2, 3, 4, 5, 6, 7, 8, 9, or more layers. Each layer surrounding the core may independently comprise the same coating material or different coating materials.

When coating the core, the coating material is formed by mixing together the raw material sources of the aliphatic monocarboxylic acids, and any other desired additives. The coating material may then be heated to above its melting point temperature so that the coating material is in a liquid state when it is applied to the core. The coating material may be heated to a temperature in the range of from about 50° C. to about 200° C., such as in the range of about 70° C. to about 110° C., or in the range of about 90° C. to about 120° C., or in the range of about 100° C. to about 160° C., or in the range of about 80° C. to about 105° C., or in the range of about 100° C. to about 150° C. After application of the liquid coating material to the core, the coated core is allowed to cool so that the coating material solidifies forming a solid layer surrounding the core. This process may be repeated one or more times to produce multiple layers of coating materials surrounding the core.

If consecutive layers of the same coating material are applied to the core as described above, the individual layers may not be distinguishable in the final product. However, the multilayering process described above imparts distinctive structural characteristics to the final product when compared to a product surrounded by a single layer of the same coating material having the same thickness as the coat of the multilayered product. While the liquid coating material is allowed to cool and solidify into a solid layer, defects such as micro-fissures, cracks, and pores may form in the layer. These defects can create paths for the ruminal environment to access and start degrading the core. Although any additional layers may also exhibit such defects, the defects in one layer may be offset by non-defect areas in a coating layer above or below and in direct contact with said one layer. Thus, by applying multiple layers of coating material to the core, where each layer is allowed to cool and solidify before fanning the next layer, the number of defects that run continuously or create a path from the outer surface of the outermost layer to the core decreases.

The number and size of the defects in a layer may vary depending on the core size, coating materials, the coating process, and the process parameters utilized for making the coated core. As such, the number of layers and the thickness of each layer necessary to obtain a desired bypass rate and intestinal digestibility rate may vary depending upon the variables selected.

The coated core materials may then be used as a feed supplement or feed additive. Appropriate amounts of the coated granules are added to the ruminant feed, for example by mixing. When the feed supplement is ingested by the ruminant, the physiologically active substance is stably delivered past the rumen at a bypass rate as described above, such that a percentage of the active substance is delivered past the rumen for digestion and take up into the ruminant's system. In the case of lysine sulfate, the feed supplement should be added to the ruminant feed in an amount that would provide between about 5 to 120 grams of lysine sulfate per head of cattle per day.

EXAMPLES

Comparative Example 300 grams of granulated lysine sulfate (BIOLYS®, Evonik Corporation), having granules with a diameter in a range of 0.3 mm to 1.6 mm, was heated by thermal conduction to 43° C., and then transferred to a low shear mixer. While agitating the lysine sulfate under low shear, 33% by volume of a pre-measured amount of hydrogenated soybean oil ($T_m$=49° C.) heated to a temperature of 93° C. was added to the mixer using continuous pour, coating the lysine sulfate. No supplemental compounds were added. The product, while under agitation, was allowed to cool to 43° C. Hydrogenated soybean oil heated to a temperature of 93° C. was again added until the product temperature reached 54° C., and the product, while under agitation, was allowed to cool to 43° C. The cycle was repeated once more, completing the addition of hydrogenated soybean oil. The final product had a 60% core to 40% coating by weight.

Approximately 10 grams of the test product was weighed into 5 cm×10 cm bags (ANKOM #510, average pore size of 50±15 microns). Each bag was heat sealed twice. A total of 5 bags of the test product was prepared for each cow plus 4 blank bags. Each bag was labeled sequentially using a permanent marker and sample information was recorded on log sheets. A sample of the test product was collected and analyzed for initial dry matter (DM) and nitrogen (N) content.

Immediately before insertion into the rumen, the bags were soaked in 39° C. water for approximately five minutes to wet the test material. The bags were then inserted into the rumen of three lactating Holstein cows previously fitted with rumen cannula. After an incubation period of 16 hours, the bags were removed from the rumen and immediately placed in ice water until they were washed three times. After washing, the bags were dried at 45° C. Once dry, each bag and its residue was weighed to determine the amount of dry matter (DM) escaping ruminal degradation using the following formula:

$$\% \text{ DM escape} = \frac{\text{mass of initial sample} - \text{mass of sample residue}}{\text{mass of initial sample}} \times 100$$

The rumen bypass rate (% DM escape) for the test product was 75.17% with a 2.85% standard deviation.

Examples 1-21

300 kilograms of granulated lysine sulfate (BIOLYS®, Evonik Corporation), having granules with a diameter of 0.3 mm to 1.6 mm, was added to a fluidized coating chamber and heated to 43° C. by using 53° C. heated air to fluidize the chamber. Once the substrate reached initial product temperature, coating material preheated to a temperature of 120° C. was applied through the fluid air stream to reach a product application temperature of 55° C. As per the design of a fluidized coater, material moves in and out of the coating stream, building up successive layers. The air inlet temperature was controlled to maintain a product temperature of 55° C. until all of the pre-weighed coating mixture was applied to achieve a 55% core to 45% coating by weight, The product was then cooled in the fluidized air chamber until ambient temperature (25° C.) was reached.

Table 1 below summarizes the data obtained for Examples 1-21 that were produced using a fluid bed process similar to that described above. These examples illustrate a variety of different combinations of product parameters.

TABLE 1

| Example | wt % Lysine Sulfate | wt % Hydrogenated Rapeseed Oil | wt % Supplemental Compound(s) | % of Lysine Sulfate > X μm | d₅₀ of Final Product (μm) |
|---|---|---|---|---|---|
| 1 | 60% | 36% | 4% stearic acid | 100% > 600 μm | 1387 |
| 2 | 60% | 36% | 4% stearic acid | 99.9% > 600 μm | 1369 |
| 3 | 60% | 36% | 4% stearic acid | 99.8% > 800 μm | 1417 |
| 4 | 60% | 36% | 4% stearic acid | 99.9% > 600 μm | 1060 |
| 5 | 60% | 36% | 4% oleic acid | 100% > 600 μm | 1356 |
| 6 | 60% | 38% | 2% lecithin | 100% > 600 μm | 1353 |
| 7 | 60% | 38% | 2% lecithin | 99.9% > 600 μm | 1346 |
| 8 | 60% | 38% | 2% oleic acid | 99.2% > 800 μm | 1420 |
| 9 | 60% | 38% | 2% oleic acid | 99.2% > 800 μm | 1440 |
| 10 | 60% | 36% | 2% stearic acid 2% lecithin | 99.9% > 600 μm | 1325 |
| 11 | 60% | 36% | 2% oleic acid 2% lecithin | 100% > 600 μm | 1519 |
| 12 | 60% | 36% | 2% stearic acid 2% oleic acid | 99.4% > 800 μm | 1431 |
| 13 | 50% | 50% | n/a | 99.5% > 800 μm | 1457 |
| 14 | 55% | 45% | n/a | 100% > 600 μm | 1347 |
| 15 | 55% | 43% | 2% lecithin | 99.9% > 600 μm | 1343 |
| 16 | 55% | 43% | 2% oleic acid | 99.6% > 800 μm | 1416 |
| 17 | 60% | 38% | 2% palm oil | 100% > 600 μm | 1384 |
| 18 | 60% | 36% | 4% palm oil | 100% > 600 μm | 1400 |
| 19 | 60% | 36% | 2% palm oil 2% lecithin | 100% > 600 μm | 1292 |
| 20 | 60% | 36% | 2% palm oil 2% stearic acid | 99.9% > 600 μm | 1259 |
| 21 | 55% | 41% | 4% stearic acid | 99.9% > 600 μm | 1297 |

Examples 22-31

Examples 22-31 were produced using a fluid bed process substantially similar to that described above. Each of Examples 22-31 was analyzed for rumen bypass rate (% DM escape). Some of the example products were further analyzed to determine the intestinal digestibility rate of nitrogen by an in vivo digestibility test.

Rumen Bypass Protocol

Approximately 20 grams of test product was weighed into 5 cm×10 cm bags (ANKOM #510, average pore size of 50±15 microns). Each bag was heat sealed twice. A total of 20 bags of test product was prepared for each cow plus 2 blank bags. Each bag was labeled sequentially using a permanent marker and sample information was recorded on log sheets. A sample of the test product was collected and analyzed for initial dry matter (DM), nitrogen (N), and lysine content.

Immediately before insertion into the rumen, the bags were soaked in 39° C. water for approximately five minutes to wet the test material. The bags were then inserted into the rumen of lactating Holstein cows previously fitted with rumen cannula. After an incubation period of 16 hours, the bags were removed from the rumen and immediately placed in ice water until they were washed three times. After washing, the bags were dried at 45° C. Once dry, each bag and its residue was weighed to determine the amount of dry matter (DM) escaping ruminal degradation using the following formula:

$$\% \ DM \ \text{escape} = \frac{\text{mass of initial sample} - \text{mass of sample residue}}{\text{mass of initial sample}} \times 100$$

In Vivo Intestinal Digestibility Test Protocol

The intestinal digestibility rate was determined by an in vivo digestibility test. The protocol is based on the recommendations published in National Research Council, "Nutrient requirements of dairy cattle," 7th rev. ed., Natl. Acad. Sci., Washington, D.C., (2001), incorporated herein by reference. Approximately 0.8 grams of test product was weighed into 5 cm×10 cm bags (ANKOM #510, average pore size of 50±15 microns). Each bag was heat sealed twice. The bags were soaked in pepsin/HCl solution (100 mg pepsin per liter of 0.01 N HCl) for 2 hours at 39° C. in a shaking water bath. Enough HCl was added to decrease the pH to 2.4. The bags were rinsed with distilled water and kept at −18° C. until introduction into the duodenum. One bag was inserted into the duodenal cannula each day every 15 minutes following a meal for a 3 hour period (total of 12 bags per cow). The bags were collected from the feces from 8 to 20 hours after initial insertion. Upon recovery, the bags were rinsed under tap water until the rinse water was clear. The bags were dried at 55° C. and residue pooled by replicate and the tested product was analyzed for DM and N content. The apparent intestinal digestibility of nitrogen was calculated using the following formula:

$$\% \ N \ \text{digestibility} = \frac{\text{mass of initial sample } N - \text{mass of residue } N}{\text{mass of initial sample } N} \times 100$$

The results for Examples 22-31 are summarized in Table 2.

TABLE 2

| Example | wt % Lysine Sulfate | wt % HVO | Type HVO | Wt % Oleic Acid | Wt % Stearic Acid | Ruminal DM Escape % | Duodenal N Digestibility % |
|---|---|---|---|---|---|---|---|
| 22 | 60 | 36 | Soybean | 4 | 0 | 91.9 | n/a |
| 23 | 60 | 36 | Soybean | 4 | 0 | 88.2 | 88.7 |
| 24 | 60 | 36 | Soybean | 4 | 0 | 92.0 | 96.8 |
| 25 | 55 | 43 | Soybean | 2 | 0 | 87.5 | n/a |
| 26 | 60 | 36 | Soybean | 2 | 2 | 91.2 | n/a |
| 27 | 60 | 36 | Rapeseed | 0 | 4 | 87.4 | 74.5 |
| 28 | 55 | 41 | Rapeseed | 0 | 4 | 97.8 | n/a |
| 29 | 55 | 43 | Rapeseed | 2 | 0 | 92.2 | 99.0 |
| 30 | 60 | 36 | Rapeseed | 4 | 0 | 78.5 | |
| 31 | 60 | 36 | Rapeseed | 2 | 2 | 88.6 | 98.9 |

Examples 32-51

Table 3 below summarize the fatty acid profiles of Examples 32-51, where coating materials comprising at least 93% by weight of saturated fatty acids were obtained using various mixtures of different raw materials.

TABLE 3

| | Raw Materials (wt % of total weight of composition) | | | | Fatty Acid Profile of Coating Material (wt % of total weight of coating) | | | |
|---|---|---|---|---|---|---|---|---|
| | Coating Materials | | | | | | | |
| Example | AP 660 | 95% Palmitic Acid | 90% Stearic Acid | Liquid Oleic Acid | Core Lysine Sulfate | Palmitic Acid | Stearic Acid | Other Saturated Fatty Acids | Total Saturated Fatty Acids |
| 32 | 0 | 9 | 35 | 1 | 55 | 20.9 | 75.2 | 2.0 | 98.1 |
| 33 | 0 | 6 | 38 | 1 | 55 | 15.4 | 80.6 | 2.1 | 98.1 |
| 34 | 0 | 4 | 40 | 1 | 55 | 10.4 | 85.7 | 2.0 | 98.1 |
| 35 | 0 | 9 | 33 | 3 | 55 | 21.2 | 71.5 | 2.0 | 94.8 |
| 36 | 0 | 6 | 36 | 3 | 55 | 16.3 | 75.8 | 1.9 | 94.1 |
| 37 | 0 | 4 | 38 | 3 | 55 | 11.1 | 81.0 | 2.1 | 94.2 |
| 38 | 37 | 7 | 0 | 1 | 55 | 21.7 | 72.7 | 3.2 | 97.7 |
| 39 | 40 | 4 | 0 | 1 | 55 | 16.1 | 78.3 | 3.3 | 97.7 |
| 40 | 42 | 2 | 0 | 1 | 55 | 10.3 | 84.2 | 3.3 | 97.8 |
| 41 | 35 | 7 | 0 | 3 | 55 | 15.3 | 75.1 | 3.4 | 93.8 |
| 42 | 38 | 4 | 0 | 3 | 55 | 10.6 | 79.7 | 3.4 | 93.7 |
| 43 | 40 | 2 | 0 | 3 | 55 | 21.5 | 68.8 | 3.3 | 93.5 |
| 44 | 34 | 7 | 0 | 1 | 58 | 21.7 | 72.6 | 3.3 | 97.5 |
| 45 | 37 | 4 | 0 | 1 | 58 | 15.8 | 78.5 | 3.4 | 97.7 |
| 46 | 39 | 2 | 0 | 1 | 58 | 10.6 | 83.7 | 3.4 | 97.7 |
| 47 | 32 | 7 | 0 | 3 | 58 | 21.4 | 68.8 | 3.3 | 93.5 |
| 48 | 35 | 4 | 0 | 3 | 58 | 15.5 | 74.9 | 3.4 | 93.7 |
| 49 | 37 | 2 | 0 | 3 | 58 | 10.5 | 79.6 | 3.5 | 93.7 |
| 50 | 19 | 5 | 18 | 3 | 55 | 15.1 | 76.2 | 2.6 | 93.8 |
| 51 | 25 | 5 | 12 | 3 | 55 | 15.5 | 75.2 | 2.9 | 93.6 |

It will be appreciated that various of the above-disclosed and other features and functions, or alternatives thereof, may be desirably combined into many other different systems or applications. Also, variously presented unforeseen or unanticipated alternatives, modifications, variations, or improvements therein may be subsequently made by those skilled in the art, and are also intended to be encompassed by the following claims.

What is claimed is:

1. A ruminant feed composition, comprising:
a granulated core comprising lysine sulfate; and
a coating material surrounding the core, the coating material comprising;
oleic acid,
stearic acid, and
palmitic acid;
wherein the total amount of stearic and palmitic acids is at least 90 wt % of the total weight of the coating, and
wherein the lysine exhibits a rumen bypass rate greater than 75%, and an intestinal digestibility rate greater than 70%.

2. The composition of claim 1, wherein the core is surrounded by two or more layers of coating material.

3. The composition of claim 2, wherein the granulated core material has a granular size of about 0.3 mm to about 3.0 mm.

4. The composition of claim 3, wherein the weight % ratio of core material to coating material is from 58:42.

5. The composition of claim 3, wherein the weight % ratio of core material to coating material is from 55:45.

6. The composition of claim 4, wherein the coating material has a melting temperature in the range of from about 50° C. to about 80° C.

7. The composition of claim 6, wherein the composition exhibits an intestinal digestibility rate of at least 80%.

8. The composition of claim 7, wherein the composition exhibits rumen bypass rate of at least 80%.

9. The composition of claim 2, wherein the granulated core material has a granular size of about 0.3 mm to about 3.0 mm.

10. The composition of claim 9, wherein the weight % ratio of core material to coating material is 55:45.

11. The composition of claim 10, wherein the coating material has a melting temperature in the range of from about 50° C. to about 80° C.

12. The composition of claim 11, wherein the composition exhibits rumen bypass rate of at least 80%.

13. The composition of claim 12, wherein the composition exhibits an intestinal digestibility rate of at least 80%.

14. A method of supplementing the diet of a ruminant with lysine, the method comprising:
providing the ruminant with a ruminant feed composition comprising:
a granulated core comprising lysine sulfate; and
a coating material of two or more layers surrounding the core, the coating material comprising;
oleic acid,
stearic acid, and
palmitic acid;
wherein the total amount of stearic and palmitic acids is at least 90 wt % of the total weight of the coating,
wherein the lysine exhibits a rumen bypass rate greater than 75%, and an intestinal digestibility rate greater than 70%, and
wherein the weight % ratio of core material to coating material is from 50:50 to 70:30.

15. The method of claim 14, wherein the lysine exhibits a rumen bypass rate greater than 80%, and an intestinal digestibility rate greater than 80%, and wherein the weight % ratio of core material to coating material is 55:45.

16. The method of claim 14, wherein the lysine exhibits a rumen bypass rate greater than 80%, and an intestinal digestibility rate greater than 80%, and wherein the weight % ratio of core material to coating material is 58:42.

17. A method of making an encapsulated ruminant feed composition, the method comprising:

obtaining a core comprising lysine sulfate;

combining oleic acid, stearic acid, and palmitic acid to form a coating material;

heating the coating material to between 50 and 80 degrees Celsius;

applying the heated coating material to the core to form a continuous layer of coating material;

allowing the layer of coating material to solidify to create an encapsulated core.

18. The method of claim 17, further comprising:

applying a second layer of coating material to the encapsulated core.

19. The method of claim 17, wherein the weight % ratio of core material to coating material is from 50:50 to 70:30.

20. The method of claim 19, wherein the weight % ratio of core material to coating material is 55:45, and wherein the coating material comprises soybean oil.

21. The method of claim 19, wherein the weight % ratio of core material to coating material is 58:42, and wherein the coating material comprises soybean oil.

* * * * *